United States Patent [19]

Zasloff

[11] Patent Number: 5,254,537
[45] Date of Patent: Oct. 19, 1993

[54] COMPOSITION AND TREATMENT WITH PEPTIDE COMBINATIONS

[75] Inventor: Michael Zasloff, Merion Station, Pa.

[73] Assignee: The Children's Hospital of Pennsylvania, Philadelphia, Pa.

[21] Appl. No.: 711,183

[22] Filed: May 10, 1991

Related U.S. Application Data

[63] Continuation-in-part of Ser. No. 346,894, May 3, 1989, abandoned, which is a continuation-in-part of Ser. No. 302,985, Jan. 30, 1989, abandoned.

[51] Int. Cl.$^5$ .............................................. A61K 37/02
[52] U.S. Cl. ...................................... 514/13; 514/12; 514/14
[58] Field of Search ............................ 514/12, 13, 14

[56] References Cited

PUBLICATIONS

M. Zasloff, "Magainins, a class of antimicrobial peptides from Xenopus skin: Isolation, characterization of two active forms, and partial cDNA sequence of a precursor," *Proc. Natl. Acad. Sci.*, vol. 84, pp. 5449–5453 (Aug. 1987).

W. Hoffmann et al., "A novel peptide designated PYLa and its precursor as predicted from cloned mRNA of *Xenopus laevis* skin," *EMBO J.* 2:711–714, 1983.

Andreu et al., *J. Biochem.* 149:531–535, 1985.

Gibson et al., "Novel Peptide Fragments Originating from PGLa and the Caeruleinand Xenopsin Precursors from *Xenopus laevis*," *J. Biol. Chem.* 261:5341–5349, 1986.

Giovannini, et al., "Biosynthesis and degradation of peptides derived from *Xenopus laevis* prohormones," *Biochem. J.* 243:113–120, 1987.

*Primary Examiner*—Michael G. Wityshyn
*Assistant Examiner*—Choon P. Koh
*Attorney, Agent, or Firm*—Woodcock Washburn Kurtz Mackiewicz & Norris

[57] ABSTRACT

A composition comprising a magainin peptide or an analogue or derivative thereof, and at least one member selected from the group consisting of a PGLa peptide or analogue or derivative thereof, and an XPF peptide or analogue or derivative thereof. The composition is employed as a pharmaceutical.

26 Claims, No Drawings

COMPOSITION AND TREATMENT WITH PEPTIDE COMBINATIONS

This application is a continuation-in-part of Application Ser. No. 346,894, filed May 3, 1989, now abandoned which is a continuation-in-part of Application Ser. No. 302,985, filed Jan. 30, 1989 now abandoned.

This invention relates to biologically active peptides, and more particularly to compositions and uses involving combinations of biologically active peptides.

In accordance with an aspect of the present invention, there is provided a composition which includes (a) a magainin peptide or analogue or derivative thereof; and (b) at least one member selected from the group consisting of (i) a PGLa peptide or analogue or derivative thereof and (ii) an XPF peptide or analogue or derivative thereof. The magainin peptide or analogue or derivative thereof, as well as the PGLa peptide or analogue or derivative thereof and the XPF peptide or analogue or derivative thereof, may be amide terminated or carboxy-terminated.

In accordance with another aspect of the present invention, there is provided a process which comprises administering to a host both (a) a magainin peptide or analogue or derivative thereof and (b) at least one member selected from the group consisting of (i) an XPF peptide or analogue or derivative thereof and (ii) a PGLa peptide or analogue or derivative thereof. In one embodiment, components (a) and (b) may be administered in separate compositions. In another embodiment, components (a) and (b) may be administered in a single composition. In addition, components (a) and (b) may be administered in amounts effective to inhibit growth of a target.

Although the present invention is not to be limited by any theoretical reasoning, it is believed that the combination of the magainin peptide with the PGLa peptide or XPF peptide provides a synergistic effect in the inhibition of growth of a target. The target, for example, may be bacteria, fungi, protozoa, virally infected cells, malignant cells, or sperm cells as compared to normal host cells. The synergism may be due to association of the peptides to a novel multimeric complex, such as a dimer, which possesses markedly increased membrane affinity for the target cells. The complex formed between the two peptides is believed to possess potent membrane disruptive properties. It is believed that the peptides have the capacity to organize within target cell membranes and to disturb cellular functions.

In general, the magainin peptide or analogue or derivative thereof is employed in a dosage of from about 1mg to about 100 mg per kilogram of host weight, when administered systemically. When administered topically, the magainin peptide is used in a concentration of from about 0.5% to about 0.50%.

The PGLa peptide or analogue or derivative thereof, when administered systemically, is administered in a dosage of from about 1 mg to about 100 mg per kilogram of host weight. When administered topically, the PGLa peptide is administered in a concentration of from about 0.5% to about 0.50%.

The XPF peptide or analogue or derivative thereof, when administered systemically, is administered in a dosage of from about 1 mg to about 100 mg per kilogram of host weight. When administered topically, the XPF peptide or analogue or derivative thereof is administered in a concentration of from about 0.05% to about 0.50%.

The use of this combination of peptides in accordance with the present invention is effective as an antibiotic, and may be employed to inhibit, prevent or destroy the growth or proliferation of microbes, such as bacteria, fungi, or the like. Similarly, such compositions may be employed as an anti-viral composition to inhibit, prevent or destroy the growth or proliferation of viruses or virally-infected cells.

Such compositions may also be employed as a spermicide to inhibit, prevent or destroy the motility of sperm.

Such compositions may also be employed as anti-tumor agents to inhibit the growth of or destroy tumors.

The compositions have a broad range of potent antibiotic activity against a plurality of microorganisms, including gram-positive and gram-negative bacteria, fungi, protozoa and the like. Such compositions may be employed for treating or controlling microbial infection caused by organisms which are sensitive to such composition. The treatment may comprise administering to a host organism or tissues acceptable to or affiliated with a microbial infection an anti-microbial amount of magainin peptide or analog or derivative thereof and of PGLa peptide or XPF peptide.

The compositions may also be used as preservatives or sterilants for materials susceptible to microbial contamination.

The magainin peptide may be, for example, a magainin such as magainin I, II or III or an analogue or derivative thereof. The magainin peptides preferably include the following basic peptide structure $X_{12}$

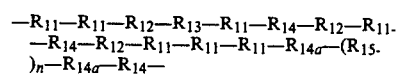

wherein $R_{11}$ is a hydrophobic amino acid, $R_{12}$ is a basic hydrophilic amino acid; $R_{13}$ is a hydrophobic, neutral hydrophilic or basic hydrophilic amino acid; $R_{14}$ and $R_{14a}$ are hydrophobic or or a hydrophobic or basic hydrophilic amino acid, and n is 0 or 1. In a preferred embodiment, $R_{13}$ is a hydrophobic or neutral hydrophilic amino acid, $R_{14a}$ is a hydrophobic amino acid, and $R_{15}$ is glutamic acid or aspartic acid.

The hydrophobic amino acids may be selected from the class consisting of Ala, Cys, Phe, Gly, Ile, Leu, Met, Val, Trp, and Tyr. The neutral hydrophilic amino acids may be selected from the class consisting of Asn, Gln, Ser, and Thr. The basic hydrophilic amino acids may be selected from the class consisting of Lys, Arg, and His, Orn, homoarginine (Har), 2,4-diaminobutyric acid, and p-aminophenylalamine.

The magainin peptides generally include preferably at least seventeen amino acids and may also include up to forty amino acids. Accordingly, the hereinabove described basic peptide structure of a magainin peptide may include additional amino acids at the amino end or at the carboxyl end, or at both ends.

Thus, for example, a magainin peptide may include the following structure:

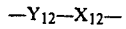

where $X_{12}$ is the hereinabove described basic peptide structure and $Y_{12}$ is
(i) $R_{12}$
ii) $R_{14a}—R_{12}$ (iii) $R_{11}-R_{14a}-R_{12}$
(iv) $R_{14}-R_{11}-R_{14a}-R_{12}$ wherein $R_{11}$, $R_{12}$, $R_{14}$ and $R_{14a}$ are as previously defined.

A magainin peptide may also have the following structure $$-X_{12}-Z_{12}-$$

wherin $X_{12}$ is as previously defined and $Z_{12}$ is:
(i) $R_{16}$ where $R_{16}$ is a basic hydrophilic amino acid or asparagine or glutamine.
(ii) $R_{16}-R_{17}$ where $R_{17}$ is a neutral hydrophilic amino acid, a hydrophobic amino acid, or a basic hydrophilic amino acid. Preferably $R_{17}$ is a neutral hydrophilic amino acid.

A magainin peptide may also have the following structure:

$$(Y_{12})_a-X_{12}-(Z^{12})_b$$

where $X_{12}$, $Y_{12}$ and $Z_{12}$ are as previously defined and a is 0 or 1 and b is 0 or 1.

The magainin peptides may also include the following basic peptide structure $X_{13}$:

$$-R_{14}-R_{11}-R_{14a}-R_{12}-R_{11}-R_{11}-R_{12}-R_{13}-R_{11}-R_{14}-R_{12}-R_{11}-R_{11}-R_{12}-,$$

wherein $R_{11}$, $R_{12}$, $R_{13}$, $R_{14}$, and $R_{14a}$ are amino acids as hereinabove described.

The magainin peptide may also include the following structure $X_{13}-Z_{13}$; wherein $X_{13}$ is the hereinabove described basic peptide structure and $Z_{13}$ is $$(R_{11})_n-(R_{11})_n-(R_{11})_n-(R_{14a})_n-(R_{15})_n-(R_{14a})_n-(r_{14})_n-R_{16})_n-(R_{17})_n$$

wherein $R_{11}$, $R_{14}$, $R_{14a}$, $R_{15}$, $R_{16}$, and $R_{17}$ are as hereinabove described, and n is 0 or 1, and each n may be the same or different.

The magainin peptides generally include at least fourteen amino acids and may include up to forty amino acids. A magainin peptide preferably has 22 or 23 amino acids. Accordingly, the hereinabove described basic peptide structures of a magainin peptide may include additional amino acids at the amino end or at the carboxyl end, or at both ends.

As representative examples of such magainin peptides, there may be mentioned peptides having the following primary sequences as given in the accompanying sequence listing as well as appropriate analogues and deriatives thereof:

(a) (NH$_2$) (SEQ ID NO:1) (OH) or (NH$_2$) (Magainin I)
(b) (NH$_2$) (SEQ ID NO:2) (OH) or (NH$_2$) (Magainin II)
(c) (NH$_2$) (SEQ ID NO:3) (OH) or (NH$_2$) (Magainin III)

The following are examples of peptide derivatives or analogues of the basic structure:
(d) (NH$_2$) (SEQ ID NO:4) (OH) or (NH$_2$)
(e) (NH$_2$) (SEQ ID NO:5) (OH) or (NH$_2$)
(f) (NH$_2$) (SEQ ID NO:6) (OH) or (NH$_2$)

Magainin peptides are described in *Proc. Natl. Acad Sci.* Vol 84 pp. 5449–53 (Aug. 87). The term "magainin peptides" as used herein refers to the basic magainin structure as well as derivatives and analogs thereof, including but not limited to the representative derivatives or analogs.

The peptide employed in conjunction with the magainin peptide is a PGLa peptide or an XPF peptide.

A PGLa peptide is either PGLa or an analogue or derivative thereof. The PGLa peptides preferably include the following basic structure $X_{14}$:

$$-R_{11}-R_{17}-R_{12}-R_{11}-R_{14}-R_{14}-R_{11}-R_{11}-R_{14}-R_{12}-R_{11}-R_{11}-R_{12}-R_{11}-R_{11}-R_{11}-R_{12}-$$

where $R_{11}$, $R_{12}$, $R_{14}$, and $R_{17}$ are as previously defined.

The PGLa peptides generally include at least seventeen amino acids and may include as many as forty amino acids. Accordingly, the hereinabove described basic peptide sturcture for a PGLa peptide may include additional amino acids at the amino end or at the carboxyl end or at both the amino and carboxyl end.

Thus, for example, a PGLa peptide may have the following sturcture:

$$-Y_{14}-X_{14}-$$

where $X_{14}$ is as previously defined and
$Y_{14}$ is
(i) $R_{11}$;
(ii) $R_{14}-R_{11}$
where $R_{11}$ and $R_{14}$ are as previously defined.

For example, a PGLa peptide may also have the following structure:

$$-X_{14}-Z_{14}-$$

where $X_{14}$ is as previously defined; and $Z_{14}$ is:
(i) $R_{11}$; or
(ii) $R_{11}-R_{11}$, where $R_{11}$ is as previously defined.

A PGLa peptide may also have the following structure:

$$(Y_{14})_a-X_{14}-(Z_{14})_b$$

where $X_{14}$; $Y_{14}$ and $Z_{14}$ are as previously defined, a is 0 or and b is 0 or 1.

An XPF peptide is either XPF or an analogue or derivative thereof. The XPF like peptides preferably include the following basis peptide structure $X_{16}$:

$$-R_{11}-R_{17}-R_1-R_{11}-R_{14}-R_{18}-R_{17}-R_{11}-R_{14}-R_{12}-R_{11}-R_{11}-R_{12}-R_{11}-R_{11}-R_{11}-R_{12}-(R_{15})_n-R_{11}-,$$

wherein $R_{11}$, $R_{12}$, $R_{14}$, $R_{15}$ and $R_{17}$ are as previously defined and $R_{18}$ is glutamine or asparagine, or a basic hydrophilic, or hydrophobic amino acid, and n is 0 or 1.

The XPF peptides generally include at least nineteen amino acids and may include up to forty amino acids. Accordingly, the hereinabove described basic peptide structure of XPF may include additional amino acids at the amino end, or at the carboxyl end or at both the amino and carboxyl ends.

Thus, for example, an XPF peptide may include the following structure:

$$-Y_{16}-X_{16}-$$

where $X_{16}$ is as previously defined and $Y_{16}$ is
(i) $R_{11}$ or
(ii) $R_{14}-R_{11}$ where $R_{11}$ and $R_{14}$ are as previously defined.
An XPF peptide may include the following structure:

$$-X_{16}-Z_{16}-$$

where $X_{16}$ is as previously defined and $Z_{16}$ is
(i) $R_{11}$; or
(ii) $R_{11}$—$R_{18}$; or
(iii) $R_{11}$—$R_{18}$ -Proline; or
(iv) $R_{11}$—$R_{18}$ -Proline —$R_{12}$ An XPF peptide may also have the following structure:

$$(Y_{16})_a\text{—}X_{16})(Z_{16})_b$$

where $X_{16}$, $Y_{16}$ and $Z_{16}$ are as previously defined: a is 0 or 1 and b is 0 or 1.

Preferred are XPF or PGLa peptides, which are characterized by the following primary amino acid sequences as given in the accompanying sequence listing:
PGLa: (SEQ ID NO:7) (NH$_2$)
XPF: (SEQ ID NO:8)

A review of XPF and PGLa can be found in Hoffman et al, *EMBO J.* 2:711-714, 1983; Andreu et al, *J. Biochem.* 149:531-535, 1985; Gibson et al *J. Biol. Chem.* 261:5341-5349, 1986; and Giovanni et al, *Biochem J.* 241:113-120, 1987.

The present invention will be further described with respect to the following examples, however, the scope of the present invention is not to be limited thereby.

EXAMPLE 1

About $10^5$ bacteria/ml were added to a small volume of Luria broth. Magainin 2 (MGN2), PGLa peptide, or a mixture of MGN2 and PGLa in a 1:1 molar ratio was added to the broth in increasing concentration. The minimal inhibitory concentration (MIC), which inhibits microbial growth completely at 24 hours is noted below in Table 1.

TABLE 1
ANTIBACTERIAL ACTIVITY OF
COMBINATION OF PGLa AND MAGAININ 2

| ORGANISM | MINIMAL INHIBITORY CONCENTRATION (μg/ml) | | |
|---|---|---|---|
| | MGN2 | PGLa | PGLa/MGN2 (1:1 molar ratio) |
| S. aureus | >500 | >500 | 10 |
| P. aeruginosa | 250 | 250 | 10 |
| C. albicans | 250 | 240 | 10 |
| Micrococcus | 125 | 125 | 10 |
| Diphtheroids | 125 | 125 | 10 |
| E. coli | 50 | 50 | 10 |

The above results indicate an increase in antibacterial activity when a combination of Magainin 2 and PGLa peptides is added to a culture broth of bacteria in a 1:1 molar ratio of Magainin 2 to PGLa over either peptide added alone.

EXAMPLE 2

In this example, the concentration of *S. aureus* killed by 100 μg/ml of preparations of Magainin 2, PGLa, and a preparation of Magainin 2 and PGLa in a 1:1 molar ratio is noted. It was found that a 100 μg/ml preparation of Magainin 2 does not completely kill *S. aureus* at concentrations of bacteria at less than 10 bacterial/ml. Similar results were also obtained for PGLa. The 100 μg/ml preparation of the equimolar miture of Magainin 2 and PGLa, however, achieved complete killing of a concentration of $10^5$ bacteria/ml. Thus, the equimolar mixture of Magainin 2 and PGLa achieved an increase in bactericidal potency over either peptide by greater than $10^5$.

EXAMPLE 3

Approximately $10^3$ *S aureus* bacteria were added per/ml of Luria broth. Peptide preparations containing varying molar ratio amounts of PGLa to Magainin 2 (mole PGLa/mole MGN2) were added to the broths to increasing concentration of peptide (μg/ml). The microbial inhibitory concentration (MIC), at which point no growth was evident after 24 hours was measured for each peptide preparation. The results are given in Table 2 below.

TABLE 2

| Mole PGLa/ Mole MGN2 | MIC vs. *S. aureus* (μg/ml) |
|---|---|
| 10/0 | >500 |
| 10/1 | 25 |
| 7.5/2.5 | 15 |
| 5/5 | 8 |
| 2.5/7.5 | 15 |
| 1/10 | 25 |
| 0/10 | >500 |

The above results indicate that maximum bactericidal activity is achieved when an equimolar mixture of PGLa and Magainin 2 is added to the *S. aureus* culture. It is also shown, however, that preparations containing both peptides in any molar ratio achieved greater bactericidal activity than either peptide alone.

The peptide combinations, in accordance with the present invention, may be employed for treating a wide variety of hosts. In accordance with a preferred embodiment, a host may be an animal, and such animal may be a human or non-human animal. The magainin peptide and the PGLa and/or XPF peptide may be employed together in a single composition, or in separate compositions.

The magainin peptide and PGLa and/or XPF peptide may be employed in a wide variety of pharmaceutical compositions in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. It is also contemplated that the magainin peptide and the PGLa and/or XPF peptide may be delivered or administered in different forms. The magainin peptide and PGLa and/or XPF peptide may also be used in combination with adjuvants, protease inhibitors, or compatible drugs where such a combination is seen to be desirable or advantageous in controlling infection caused by harmful microorganisms including protozoa, viruses, and the like.

The peptide(s) of the present invention may be administered to a host; in particular an animal, in an effective antibiotic and/or anti-tumor and/or anti-viral and/or anti-microbial and/or a spermicidal amount.

Numerous modifications and variations of the present invention are possible in light of the above teachings, and, therefore, within the scope of the accompanying claims, the invention may be practiced other than as particularly described.

What is claimed is:

1. A composition comprising:
    a) a magainin peptide, sequence ID. No. 1, 2, or 3, or analogue or derivative thereof, sequence ID No. 4, 5, or 6; and
    b) at least one member selected from the group consisting of (i) a PGLa peptide, sequence ID. No. 7 and (ii) an XPF peptide, sequence ID. No. 8.

2. The composition of claim 1 wherein components (a) and (b) are present in an amount effective to inhibit growth of a target cell, wherein the said target cell is a bacterium, a fungus, or a protozoan.

3. The compositions of claim 1 wherein component (b) is a PGLa peptide, sequence ID. No. 7.

4. The composition of claim 1, wherein component (b) is an XPF peptide, sequence ID. No. 8.

5. The composition of claim 2, wherein each of components (a) and (b) is present in an amount effective to inhibit growth of a target cell, which is less than if each component were administered alone to a host wherein the said target cell is a bacterium, a fungus, or a protozoan.

6. A process for inhibiting growth of a target cell, in a host wherein the said target cell is a bacterium, a fungus, or a protozoan, comprising: administering to a host both (a) a margainin peptide, sequence ID. No. 1, 2, or 3, analogue or derivative thereof, sequence ID. No. 4, 5, or 6, and (b) at least one member selected from the group consisting of (i) an XPF peptide, sequence ID. No. 8 or and (ii) a PGLa peptide, sequence ID. No. 7, wherein components (a) and (b) are present in amounts effective to inhibit growth of a target cell, virus, or virally-infected cell in a host.

7. The process of claim 6 wherein components (a) and (b) are administered in separate compositions.

8. The the process of claim 6 wherein (a) and (b) are administered in a single composition.

9. The process of claim 6 wherein the magainin peptide, sequence ID. No. 1, 2, or 3, analogue or derivative thereof, sequence ID. No. 4, 5, or 6, is administered systemically.

10. The process of claim 9 wherein the magainin peptide, sequence ID. No. 1, 2, or 3, analogue or derivative thereto, sequence ID. No. 4, 5, or 6, is administered in an amount of from about 1 mg to about 100 mg per kilogram of host body weight.

11. The process of claim 6 wherein the magainin peptide, sequence ID. No. 1, 2, or 3, analogue or derivative thereof, sequence ID. No. 4, 5, or 6, is administered topically.

12. The process of claim 11 wherein the magainin peptide, sequence ID. No. 1, 2, or 3, analogue or derivative thereof, sequence ID. No. 4, 5, or 6, is administered in a concentration of from about 0.05% to about 0.50% by weight.

13. The process of claim 6 wherein component (b) is a PGLa peptide, sequence ID. No. 7.

14. The process of claim 13 wherein the PGLa peptide, sequence ID. No. 7 is administered systemically.

15. The process of claim 14 wherein the PGLa peptide, sequence ID. No. is administered in an amount of from about 1 mg to about 100 mg per kilogram of host body weight.

16. The process of claim 13 wherein the PGLa peptide, sequence ID. No. is administered topically.

17. The process of claim 16 wherein the PGLa peptide or analogue or derivative thereof is administered in a concentration of from about 0.05% to about 0.050% by weight.

18. The process of claim 6 wherein component (b) is an XPF peptide, sequence ID. No. 8.

19. The process of claim 18 wherein the XPF peptide is administered systemically.

20. The process of claim 19 wherein the XPF peptide, sequence ID. No. 8 is administered in an amount of from about 1 mg to about 100 mg per kilogram of host body weight.

21. The process of claim 18 wherein the XPF peptide, sequence ID. No. 8 is administered topically.

22. The process of claim 21 wherein the XPF peptide, sequence ID. No. 8 is administered in a concentration of from about 0.05% to about 0.50% by weight.

23. The process of claim 6 wherein said target cell is a bacterium.

24. The process of claim 6 wherein said target cell is a fungus.

25. The process of claim 6 wherein said target cell is a protozoan.

26. The process of claim 6 wherein each of components (a) and (b) is administered in an amount effective to inhibit growth of a target cell, which is less than if each component were administered alone to a host wherein the said target cell is bacterium, a fungus or a protozoan.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 23 amino acids
( B ) TYPE: amino acid
( D ) TOPOLOGY: linear ( i i ) MOLECULE TYPE: peptide ( i x ) FEATURE:
( A ) NAME/KEY: Magainin I peptide.

( x ) PUBLICATION INFORMATION:
( A ) AUTHORS: Zasloff, Michael
( C ) JOURNAL: Proceedings of the National Academy
of Sciences
( D ) VOLUME: 84
( F ) PAGES: 5449-5453
( G ) DATE: AUG - 1987
( H ) DOCUMENT NUMBER: US 4810777
( I ) FILING DATE: 04-MAR-1987
( J ) PUBLICATION DATE: 07-MAR- 1989

( x i ) SEQUENCE DESCRIPTION: SEQ ID NO:1:

Gly Ile Gly Lys Phe Leu His Ser Ala Gly
5                       10

Lys Phe Gly Lys Ala Phe Val Gly Glu Ile
15                      20

Met Lys Ser ( 2 ) INFORMATION FOR SEQ ID NO:2:

( i ) SEQUENCE CHARACTERISTICS:
( A ) LENGTH: 23 amino acids
( B ) TYPE: amino acid
( D ) TOPOLOGY: linear ( i i ) MOLECULE TYPE: peptide ( i x ) FEATURE:
( A ) NAME/KEY: Magainin II peptide.

( x ) PUBLICATION INFORMATION:
( A ) AUTHORS: Zasloff, Michael
( C ) JOURNAL: Proceedings of the National Academy
of Sciences
( D ) VOLUME: 84
( F ) PAGES: 5449-5453
( G ) DATE: AUG - 1987
( H ) DOCUMENT NUMBER: US 4810777
( I ) FILING DATE: 04-MAR-1987
( J ) PUBLICATION DATE: 07-MAR- 1989

( x i ) SEQUENCE DESCRIPTION: SEQ ID NO:2:

Gly Ile Gly Lys Phe Leu His Ser Ala Lys
5                       10

Lys Phe Gly Lys Ala Phe Val Gly Glu Ile
15                      20

Met Asn Ser ( 2 ) INFORMATION FOR SEQ ID NO:3:

( i ) SEQUENCE CHARACTERISTICS:
( A ) LENGTH: 22 amino acids
( B ) TYPE: amino acid
( D ) TOPOLOGY: linear ( i i ) MOLECULE TYPE: peptide ( i x ) FEATURE:
    ( A ) NAME/KEY: Magainin III peptide.

( x ) PUBLICATION INFORMATION:
    ( A ) AUTHORS: Zasloff, Michael
    ( C ) JOURNAL: Proceedings of the National Academy
        of Sciences
    ( D ) VOLUME: 84
    ( F ) PAGES: 5449-5453
    ( G ) DATE: AUG - 1987
    ( H ) DOCUMENT NUMBER: US 4810777
    ( I ) FILING DATE: 04-MAR-1987
    ( J ) PUBLICATION DATE: 07-MAR- 1989

( x i ) SEQUENCE DESCRIPTION: SEQ ID NO:3:

```
Gly  Ile  Gly  Lys  Phe  Leu  His  Ser  Ala  Lys
 5                           10

Lys  Phe  Gly  Lys  Ala  Phe  Val  Gly  Glu  Ile
15                           20

Met  Asn
```

( 2 ) INFORMATION FOR SEQ ID NO:4:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( i x ) FEATURE:
        ( A ) NAME/KEY: magainin peptide.

( x ) PUBLICATION INFORMATION:
        ( A ) AUTHORS: Zasloff, Michael
        ( C ) JOURNAL: Proceedings of the National Academy
            of Sciences
        ( D ) VOLUME: 84
        ( F ) PAGES: 5449-5453
        ( G ) DATE: AUG - 1987
        ( H ) DOCUMENT NUMBER: US 4810777
        ( I ) FILING DATE: 04-MAR-1987
        ( J ) PUBLICATION DATE: 07-MAR- 1989

( x i ) SEQUENCE DESCRIPTION: SEQ ID NO:4:

```
Ile  Gly  Lys  Phe  Leu  His  Ser  Ala  Lys  Lys
 5                           10

Phe  Gly  Lys  Ala  Phe  Val  Gly  Glu  Ile  Met
15                           20

Asn  Ser
```

( 2 ) INFORMATION FOR SEQ ID NO:5:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: magainin peptide.

( x ) PUBLICATION INFORMATION:
        ( A ) AUTHORS: Zasloff, Michael
        ( C ) JOURNAL: Proceedings of the National Academy
            of Sciences
        ( D ) VOLUME: 84
        ( F ) PAGES: 5449-5453
        ( G ) DATE: AUG - 1987
        ( H ) DOCUMENT NUMBER: US 4810777
        ( I ) FILING DATE: 04-MAR-1987

-continued (J) PUBLICATION DATE: 07-MAR-1989

(xi) SEQUENCE DESCRIPTION: SEQ ID NO:5:

Gly Lys Phe Leu His Ser Ala Lys Lys Phe
5                        10
Gly Lys Ala Phe Val Gly Glu Ile Met Asn
15                       20
Ser (2) INFORMATION FOR SEQ ID NO:6:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: magainin peptide.

(x) PUBLICATION INFORMATION:
        (A) AUTHORS: Zasloff, Michael
        (C) JOURNAL: Proceedings of the National Academy
            of Sciences
        (D) VOLUME: 84
        (F) PAGES: 5449-5453
        (G) DATE: AUG - 1987
        (H) DOCUMENT NUMBER: US 4810777
        (I) FILING DATE: 04-MAR-1987
        (J) PUBLICATION DATE: 07-MAR-1989

(xi) SEQUENCE DESCRIPTION: SEQ ID NO:6:

Lys Phe Leu His Ser Ala Lys Lys Phe Gly
5                        10
Lys Ala Phe Val Gly Glu Ile Met Asn Ser
15                       20

(2) INFORMATION FOR SEQ ID NO:7:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: PGLa peptide.

(x) PUBLICATION INFORMATION:
        (A) AUTHORS: Hoffman, et al.
        (C) JOURNAL: EMBO J.
        (D) VOLUME: 2
        (F) PAGES: 711-714
        (G) DATE: 1983
        (A) AUTHORS: Andreu, et al.
        (C) JOURNAL: Journal of Biochemistry
        (D) VOLUME: 149
        (F) PAGES: 531-535
        (G) DATE: 1985
        (A) AUTHORS: Gibson, et al.
        (C) JOURNAL: J. Biol. Chem.
        (D) VOLUME: 261
        (F) PAGES: 5341-5349
        (G) DATE: 1986
        (A) AUTHORS: Giovannini, et al.
        (C) JOURNAL: Biochem J.
        (D) VOLUME: 243
        (F) PAGES: 113-120
        (G) DATE: 1987

(xi) SEQUENCE DESCRIPTION: SEQ ID NO:7:

Gly Met Ala Ser Lys Ala Gly Ala Ile Ala

-continued

```
        5                       10
Gly  Lys  Ile  Ala  Lys  Val  Ala  Leu  Lys  Ala
        15                      20

Leu
```

(2) INFORMATION FOR SEQ ID NO:8:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (ix) FEATURE:
        (A) NAME/KEY: XPF peptide.

(x) PUBLICATION INFORMATION:
        (A) AUTHORS: Hoffman, et al.l
        (C) JOURNAL: EMBO J.
        (D) VOLUME: 2
        (F) PAGES: 711-714
        (G) DATE: 1983
        (A) AUTHORS: Andreu, et al.
        (C) JOURNAL: Journal of Biochemistry
        (D) VOLUME: 149
        (F) PAGES: 531-535
        (G) DATE: 1985
        (A) AUTHORS: Gibson, et al.
        (C) JOURNAL: J. Biol. Chem.
        (D) VOLUME: 261
        (F) PAGES: 5341-5349
        (G) DATE: 1986
        (A) AUTHORS: Giovannini, et al.
        (C) JOURNAL: Biochem J.
        (D) VOLUME: 243
        (F) PAGES: 113-120
        (G) DATE: 1987

(xi) SEQUENCE DESCRIPTION: SEQ ID NO:8:

```
        5                       10
Gly  Trp  Ala  Ser  Lys  Ile  Gly  Gln  Thr  Leu 15                      20
Gly  Lys  Ile  Ala  Lys  Val  Gly  Leu  Lys  Glu

25
Leu  Ile  Gln  Pro  Lys
```